United States Patent [19]
Balakrishnan

[11] Patent Number: 4,947,684
[45] Date of Patent: Aug. 14, 1990

[54] SYSTEM AND PROCESS FOR DETECTING PROPERTIES OF TRAVELLING SHEETS IN THE MACHINE DIRECTION

[75] Inventor: Ramesh Balakrishnan, Stanford, Calif.

[73] Assignee: Measurex Corporation, Cupertino, Calif.

[21] Appl. No.: 303,477

[22] Filed: Jan. 27, 1989

[51] Int. Cl.⁵ .................... G01N 33/34; G01N 33/44
[52] U.S. Cl. ........................ 73/159; 356/431; 250/563; 364/568; 364/471; 364/473; 73/73
[58] Field of Search ................ 73/159, 73; 356/429, 356/430, 431, 238; 250/563, 252.1 A; 364/568, 471, 473

[56] References Cited
U.S. PATENT DOCUMENTS

| | | | |
|---|---|---|---|
| 2,909,660 | 10/1959 | Alexander | 73/159 |
| 3,332,279 | 7/1967 | Tompos et al. | 73/159 |
| 3,508,035 | 4/1970 | Worthley | 364/568 |
| 3,552,203 | 1/1971 | Freeh | 73/159 |
| 3,562,500 | 2/1971 | Grant | 364/568 |
| 3,610,899 | 10/1971 | Dahlin | 364/568 |
| 3,840,302 | 10/1974 | Brunton et al. | 250/563 |
| 3,914,585 | 10/1975 | Wilhelm, Jr. et al. | 73/159 |
| 4,000,402 | 12/1976 | Higham | 364/469 |
| 4,453,404 | 6/1984 | Powell et al. | 73/159 |
| 4,476,717 | 10/1984 | Murphy | 73/159 |

Primary Examiner—William A. Cuchlinski, Jr.
Assistant Examiner—Diego F. F. Gutierrez
Attorney, Agent, or Firm—Burns, Doane, Swecker, & Mathis

[57] ABSTRACT

To determine machine-direction variations in measurements of a travelling sheet during production, the sheet is repeatedly traversed with a scanning sensor and, during each traverse, measurements are taken at a plurality of locations. Then, a series of reference slice locations are selected which extend in the true cross-direction. For the reference locations, measurement values are estimated based upon actual measurements. Then, for each scan, the average of the estimated measurement values is calculated. Next, cross-directional variations in values at each slice location along selected scans are calculated by subtracting the average value from the estimated value at each location along the scan. During the next consecutive scans, machine-directional variations in the sheet property at slice locations are calculated by determining the difference between the measured value and the calculated cross-directional variation value for that slice location along the prior scan.

11 Claims, 3 Drawing Sheets

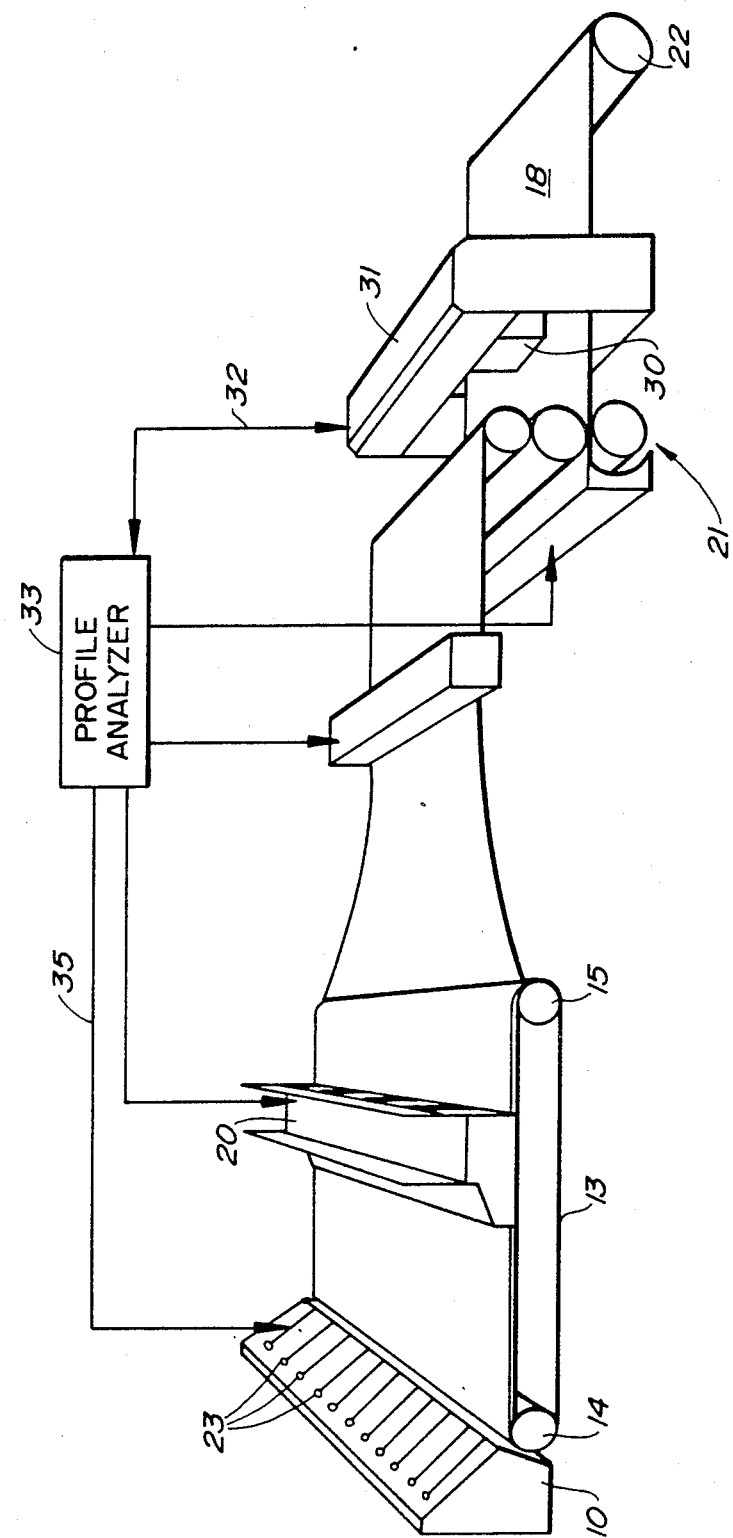
FIG._1.

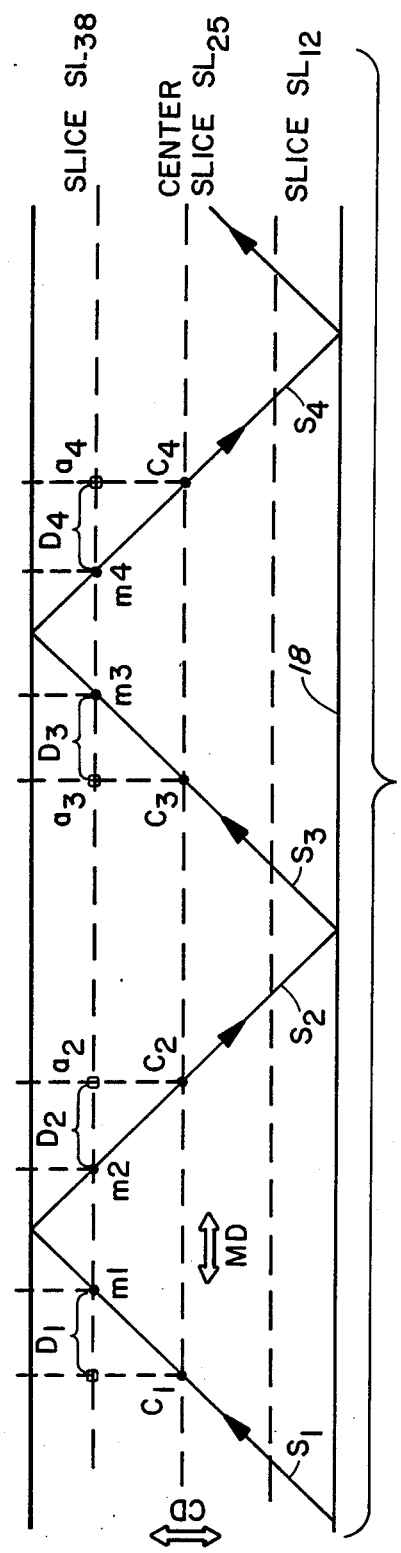
FIG._2.
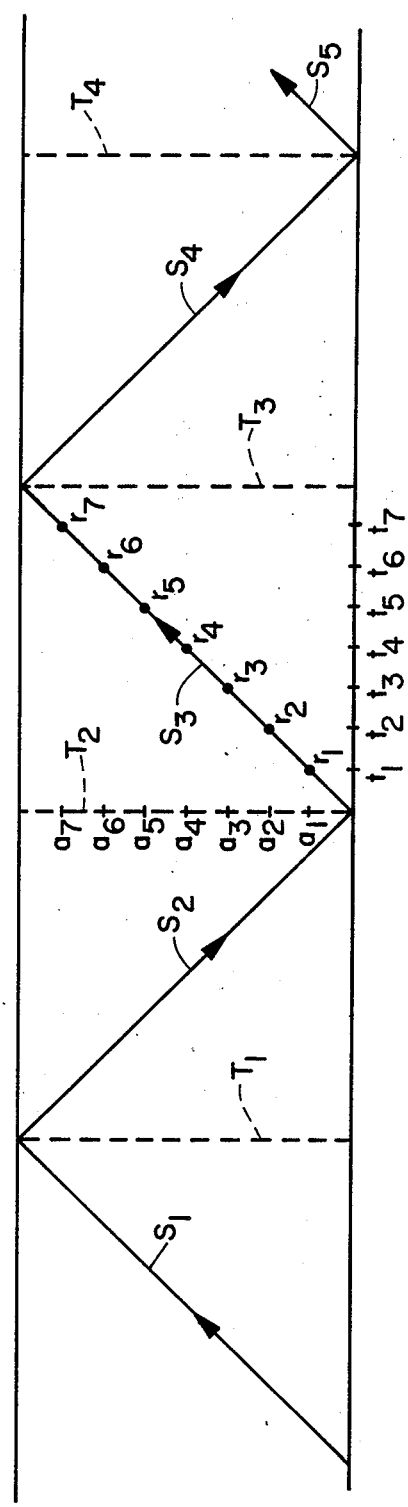
FIG._4.

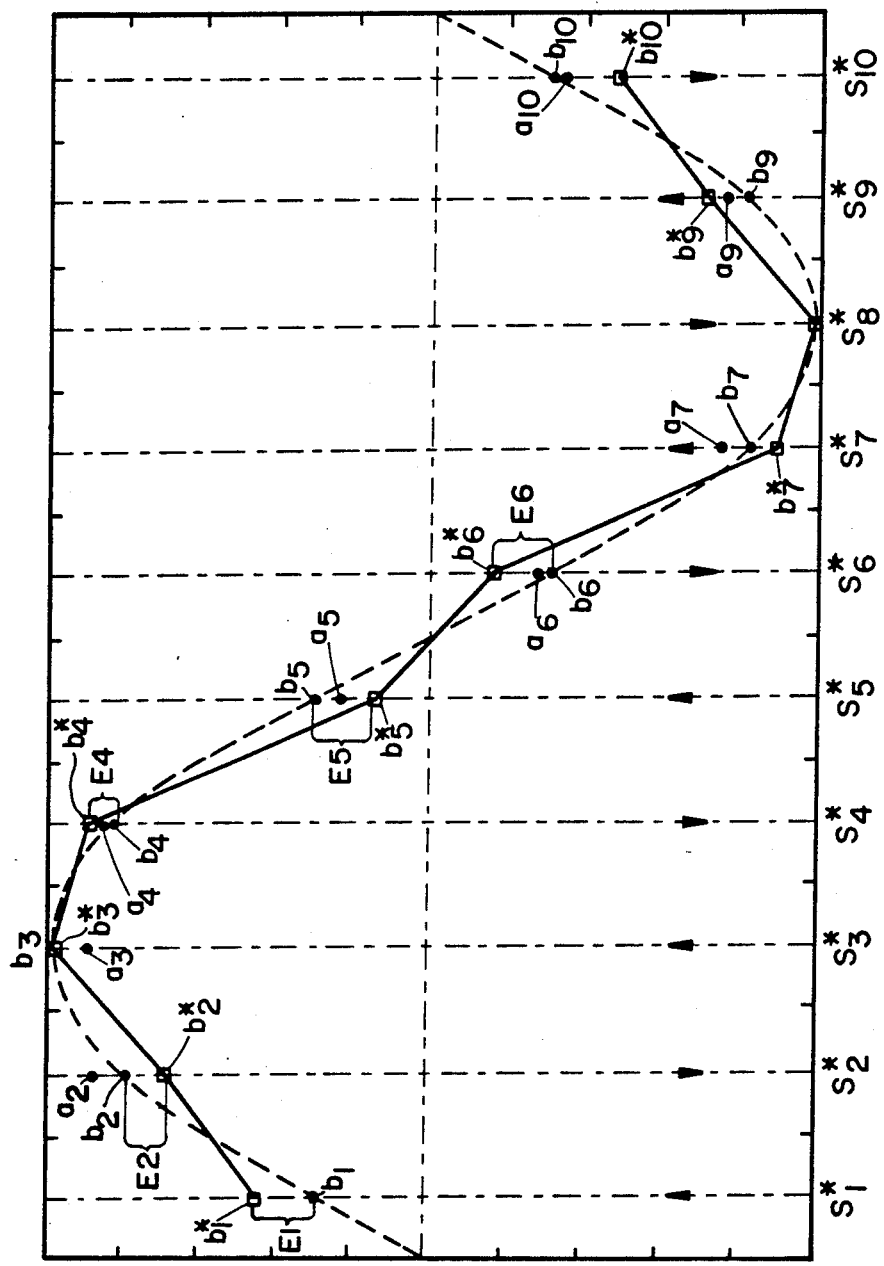
FIG._3.

SYSTEM AND PROCESS FOR DETECTING PROPERTIES OF TRAVELLING SHEETS IN THE MACHINE DIRECTION

BACKGROUND OF THE INVENTION

The present invention generally relates to sheetmaking control systems and, more particularly, to sheetmaking control systems wherein measuring devices scan across travelling sheets during sheet manufacture.

It is well known that on-line measurements can be made to detect properties of sheet materials during manufacture. Generally speaking, on-line measurements are made to enable prompt control of sheetmaking processes and, thus, to enhance sheet quality while reducing the quantity of substandard sheet material which is produced before undesirable process conditions are corrected. In the papermaking art, for instance, on-line sensors can detect variables such as basis weight, moisture content, and caliper of paper sheets during manufacture.

On-line measurements during sheetmaking are, however, difficult to make accurately. One reason for the difficulty is that many sheetmaking machines are large and operate at high speeds. For example, some modern paper-making machines produce sheets almost four hundred inches wide at rates of up to one hundred feet per second. Another factor which causes difficulty in making on-line measurements on sheetmaking machines is that the physical properties of sheet materials usually vary in the machine direction as well as in the cross direction. (In the sheetmaking art, the term "machine direction" refers to the direction of travel of sheet material during manufacture, and the term "cross direction" refers to the direction across the surface of a sheet perpendicular to the machine direction.)

To detect cross-directional variations in sheet materials, it is well known to use scanning sensors that periodically traverse back and forth across a sheetmaking machine in the cross direction while detecting values of a sheet property along each scan. The time required for a typical scan is generally between about twenty and thirty seconds for conventional high-speed scanners. The rate at which measurement readings are provided by such scanners is usually adjustably variable; a typical rate is about one measurement reading about every fifty milliseconds. Normally, measurement information provided by the scanning sensors is assembled for each scan to provide a "profile" of the detected property of the sheet in the cross direction. In other words, each profile is comprised of a succession of sheet measurements at adjacent locations extending generally in the cross direction. From such profiles, cross-directional variations in sheet properties can be detected. Based upon the detected cross-directional variations, appropriate control adjustments can be made to the sheetmaking machine.

In practice, the points at which scanning sensors make cross-directional measurements of travelling sheets are not aligned exactly perpendicular to the edges of the sheets being measured. Instead, because of sheet velocity, scanning sensors actually travel diagonally across the surface of moving sheets, with the result that consecutive scanning paths zig-zag relative to the sheet edges As a result of the zig-zag paths of scanning sensors, cross-directional profiles based on sheet measurements taken by the sensors usually include machine-direction variations. In the sheetmaking art, the term MD/CD coupling is often used to describe the combining of machine-directional and cross-directional measurements. As a result of MD/CD coupling, control systems that are intended to reduce cross-directional variations can, instead, introduce artificial control disturbances which adversely affect sheet uniformity.

In conventional practice, sheetmaking control systems often do not compensate for MD/CD coupling. However, some sheetmaking control systems do attempt to reduce, or damp, the effects of machine direction variations by time-filtering techniques. Such time-filtering techniques have several shortcomings, including the fact that they necessarily entail the loss of measurement information which might otherwise be useful.

Also in conventional practice, machinedirectional variations in sheet properties are determined only at the end of each scan. The fact that machine-directional variations are calculated on a scan-by-scan basis can lead to control limitations. For example, it is not uncommon for machine-directional properties to vary such that, within the period of a single cross-directional scan, the value of a sheet property increases and then decreases. When the machine-directional properties are calculated on a scan-by-scan basis, such relatively high frequency inter-scan variations are not detected. More specifically, it can be said that machine-direction variations in sheet properties that change at a frequency greater than one-half cycle per scan cannot be detected on a scan-by-scan basis by employing conventional techniques.

The present invention, as will be described in the following, is directed to methods to accurately detect relatively high frequency machinedirectional variations in sheet properties during production.

SUMMARY OF THE INVENTION

To determine machine-direction variations in measurements of sheet properties during production, a travelling sheet is repeatedly traversed with a scanning sensor and, during each traverse, measurements are taken at a plurality of locations. Then, a series of reference slice locations are selected which extend in the true cross-direction For the reference locations, measurement values are estimated based upon actual measurements. Then, for each scan, the average of the estimated measurement values is calculated. Next, cross-directional variations in the values at each slice location along selected scans are calculated by subtracting the average value from the estimated value at each location along the scan. During the next consecutive scan, machine-directional variations in the sheet property are calculated at the slice locations along the scan by calculating the difference between the measured value and the calculated cross-directional variation value for that slice location along the prior scan.

BRIEF DESCRIPTION OF THE DRAWINGS

FIG. 1 is a generally schematic view of an example of a conventional sheetmaking machine;

FIG. 2 is a graphical representation of a typical path traversed by a scanning sensor while measuring properties of a moving sheet;

FIG. 3 is a graph that shows actual values of a sheet property together with measured values along a particular slice of the sheet; and FIG. 4 is a graph which is provided to assist in explaining the method of the present invention.

DETAILED DESCRIPTION OF THE PREFERRED EMBODIMENT

In U.S. patent application Ser. No. 07/249,617, filed Sept. 26, 1988, and commonly assigned herewith, the disclosure of which is herein incorporated by reference, there is described a method for adjusting, or "aligning", cross-directional profile measurements of travelling sheets where the profile measurements are based upon output signals from scanning sensors. As a preliminary step in the method disclosed in the application, a sheet is repeatedly traversed with a scanning sensor and a series of reference measurement locations are selected. Normally, the reference locations are regularly spaced in the machine direction. Then, for selected locations along true cross-directional scans, measurement values are estimated. In other words, the estimated values approximate cross-directional measurement values which would have been obtained if consecutive scans had been in the true cross direction.

In the following, there is described a method for determining relatively high-frequency machine-directional variations. The methodology can employ, at least in part, the techniques suggested in the above-identified application.

FIG. 1 generally shows an example of a conventional sheetmaking machine for producing continuous sheet material. In the illustrated embodiment, the sheetmaking machine includes a feed box 10 which discharges raw material, such as paper pulp, onto a supporting web 13 trained between rollers 14 and 15. Further, the sheetmaking machine includes processing stages, such as a steambox 20 and a calendaring device 21, which operate upon the raw material to produce a finished sheet 18 which is collected onto a reel 22.

In conventional sheetmaking practice, the processing stages along the machine of FIG. 1 each include actuators for controlling the properties of sheet 18. In the illustrated embodiment, for instance, feed box 10 includes actuators 23 which control the quantity of material fed onto web 13 at adjacent cross-directional locations, normally referred to as "slices". The actuators 23 usually are independently adjustable. Similarly, steam box 20 includes actuators that control the quantity of steam applied to sheet 18 at various slice locations. Also, calendaring stage 21 can include actuators for controlling the compressive pressure applied to sheet 18 at various slice locations. In the following, the various actuators are referred to collectively as profile actuators. It should be understood that the profile actuators affect both cross-directional and machine-directional properties of the produced sheet material.

To provide control information for operating the profile actuators on the sheetmaking machine of FIG. 1, at least one scanning sensor 30 is mounted on the sheetmaking machine to measure a selected sheet property such as, for example, caliper or basis weight, during production of the sheet material. In the illustrated embodiment, scanning sensor 30 is mounted on a supporting frame 31 that extends across the sheetmaking machine in the cross direction. Further, scanning sensor 30 is connected, as by line 32, to a profile analyzer 33 for providing the analyzer with signals indicative of the magnitude of the measured sheet property at various crossdirectional measurement points. In turn, profile analyzer 33 is connected to the profile actuators at the processing stages of the sheetmaking machine for providing control signals to the actuators. For example, line 35 carries control signals from profile analyzer 33 to profile actuators 23 at feed box 10.

In operation of the system shown in FIG. 1, scanning sensor 30 periodically traverses travelling sheet 18 at generally constant speed. Because of the velocity of sheet 18, however, scanning sensor 30 does not measure the selected sheet property at locations which are aligned exactly perpendicular to the longitudinal edges of the sheet. Instead, the actual measurement locations define paths on the sheet surface which are skewed, or biased, in a zig-zag pattern with respect to the direction perpendicular to the sheet's longitudinal edges.

FIG. 2 shows an example of a pattern of actual scanning paths $S_1$, $S_2$, $S_3$, and so forth which would be traced by a scanning sensor as it traverses the surface of sheet 18 during back-and-fort consecutive scans while sheet 18 travels in the machine direction (MD). It may be appreciated that the angles of each the scanning paths relative to the true cross-direction (CD) depend upon the crossdirectional velocity of the scanning sensor and upon the machine-directional velocity of sheet 18. Also, in practice, there can be lags between the time a scanning sensor reaches an edge of a sheet and the time at which the return scan begins. Such lags can arise, for example, when the scanner goes off sheet between scans.

For convenience of discussion of the present invention, sheet 18 in FIG. 2 is shown as being divided into a series of adjacent, longitudinally extending parallel strips, referred to above as slices. Further for purposes of discussion, FIG. 2 identifies a center slice $SL_{25}$ which is midway between the longitudinal edges of the sheet, a slice $SL_{38}$ which is close to the far edge of sheet 18, and a slice $SL_{12}$ which is close to the near edge. Also in FIG. 2, the points $c_1$, $c_2$, $c_3$ and so forth indicate the points at which measurements are taken by the scanning sensor as it traverses center slice $SL_{25}$, and the points $m_1$, $m_2$, $m_3$ and so forth indicate the points at which measurements are made by the scanning sensor as it traverses slice $SL_{38}$. It should be noted that the consecutive measurement points $c_1$, $c_2$ and so forth along center slice $SL_{25}$ are evenly spaced in the machine direction, but the consecutive measurement points $m_1$, $m_2$ and so forth are not evenly spaced.

FIG. 3 is a graph of the magnitude of a measured sheet property, such as basis weight or caliper, at various locations along an off-center slice, such as slice $SL_{38}$ of FIG. 2. The vertical axis in FIG. 3 represents the magnitude of the measured sheet property, and the horizontal axis represents distance along the sheet in the machine direction. The parallel vertical lines $S_1^*$, $S_2^*$ and so forth in FIG. 3 represent the locus of crossdirectional scans which extend exactly perpendicular to the edge of sheet 18 and which would be made at regular intervals such as at the locations for the respective measurement points $c_1$, $c_2$, $c_3$ and so forth in FIG. 2. Also in FIG. 3, the arrows on the scan lines indicate the scanning direction.

For purposes of discussion of FIG. 3, it can be assumed that there is a sheet property whose magnitude is indicated by the dashed curve and that this sheet property varies generally sinusoidally in the machine direction but is constant in the cross-direction. In other words, it should be assumed that true cross-directional profile measurements for the given sheet property would be constant from slice to slice for each profile.

(Consecutive crossdirectional profiles could, however, vary.) The points labelled $b_1$, $b_2$, and so forth in FIG. 3 indicate particular values of the sheet property which would be measured for true cross-directional scans $S_1^*$, $S_2^*$, $S_3^*$ and so forth. Points $b_1^*$, $b_2^*$, $b_3^*$ and so forth in FIG. 3 indicate the magnitude of measurements which are actually obtained by scanning sensor during scans on an off-center slice such as slice $SL_{38}$. (For illustrative purposes, the points $b^*_1$, $b^*_2$, $b^*_3$ and so forth are connected by the solid line in FIG. 3.)

In other words, the values, $b_1$, $b_2$ and so forth correspond to hypothetical values of the measured sheet property for true scans, that is, scans which extend exactly perpendicular to the edge of the sheet as if the scans were made while the sheet was stationary. $S_1^*$, $S_2^*$ and so forth represent these true scans. The values $b_1$, $b_2$ and so forth differ from material to material, and their representation in FIG. 3 is solely to demonstrate examples of values which might be measured in a true scan. In view of the explanation provided below, it will be appreciated that the values $b_1$, $b_2$ and so forth have no bearing on the determination of the estimated or aligned values.

Since a scanning sensor does not travel in the true cross direction, the locations for measurements $b_1^*$, $b_2^*$, $b_3^*$ and so forth in FIG. 3 are displaced in the machine direction from the locations for measurements $b_1$, $b_2$, and so forth. Accordingly, when a sheet property varies in the machine direction, the magnitude of each of the actual measured values $b_1^*$, $b_2^*$, and so forth differs from each of the corresponding values $b_1$, $b_2$ and so forth which would have been obtained for true crossdirectional scans.

In the co-pending U.S. patent application identified above, methods are described for estimating "aligned" cross-directional measurements at regularly spaced intervals in the machine direction. In FIG. 3, examples of aligned values are indicated at points $a_2$, $a_3$, $a_4$ and so forth. The estimated measurements $a_2$, $a_3$, $a_4$ and so forth are called aligned values because they represent estimated measurement values at points which are aligned in the cross direction with the machinedirectional locations of measurements along a reference slice.

Generally speaking, the aligned values $a_2$, $a_3$ and so forth are closer in value to the actual value of a sheet property for a true crossdirectional scan than the measured values. For example, in terms of FIG. 3, point $a_2$ is closer to point $b_2$ than $b_2^*$, point $a_5$ is closer to point $b_5$ than is point $b_5^*$, and so forth for most of the other sets of points. In a practical sense, the aligned values can be understood to represent improved estimates of true cross-directional measurements.

In accordance with the present invention, estimates of machine-directional variations in a sheet property are obtained at each of a plurality of individual points along cross-directional scans. In the preferred embodiment, as will now be explained, the estimated machine-directional variations are obtained by calculations based upon cross-directional values which are aligned in the true cross-direction.

In FIG. 4, the zig-zag lines $S_1$, $S_2$ and so forth indicate a typical path traversed by a scanning sensor while measuring properties of a travelling sheet. Also in FIG. 4, true cross-directional scanning paths are indicated by the dashed vertical lines $T_1$, $T_2$, $T_3$ and so forth. The points $r_1$, $r_2$, $r_3$ and so forth along the scanning line indicate points at which measurement readings are actually taken, and those readings correspond to measurement times $t_1$, $t_2$, $t_3$ and so forth. According to the method described above and in the co-pending application, the actual readings serve as a basis for computing aligned readings $a_1$, $a_2$, $a_3$ and so forth on the true cross-directional scanning paths. To determine cross-directional variations in the sheet property, the following algorithm is used:

$$CD_{j,i} = A_{j,i} - \overline{A}_{j,i} \qquad (1)$$

In this equation, the expression $CD_{j,i}$ represents the cross-directional variation for the measurement at the $i$th slice location along the $j$th scan. The expression $A_{j,i}$ represents the aligned measurement value for the $i$th slice along the $j$th scan. The expression $\overline{A}_{j,i}$ represents the average of aligned values over the $j$th scan. To determine machines directional variations in the sheet property, the following algorithm can be used:

$$MD_{j+1,i} = R_{j+1,i} - CD_{j,i} \qquad (2)$$

In the equation, $MD_{j+1,i}$ represents the machinedirectional variation of the $i$th slice reading along the scan $j+1$. $R_{j+1,i}$ represents the measured value at the $i$th slice along the scan $j+1$.

In summary, the above-described method provides estimates for machine-directional variations at measurement points within cross-directional scans. In practice, the estimates are the basis for identifying and correcting relatively high-frequency machine-directional variations in sheet properties.

As an alternative and somewhat simpler methodology, estimated or aligned values of a sheet property can be computed as follows:

$$E_{1,i} = \tfrac{1}{2}(S_{1,i} + S_{2,i})$$

$$E_{2,i} = \tfrac{1}{2}(S_{2,i} + S_{3,i})$$

$$E_{3,i} = \tfrac{1}{2}(S_{3,i} + S_{4,i})$$

and so forth, so that $$E_{j,i} = \tfrac{1}{2}(S_{j,i} + S_{j+1,i}) \qquad (3)$$

where S represents a measurement (actual) of a sheet property and E represents an estimate of the value of the sheet property.

In the above formulation, the subscript i again identifies slice location and the subscript j indicates the scan number. Thus, the expression $S_{36}$, for example, represents the value of a measurement (actual) of a sheet property at the sixth slice on the third scan.

According to the method described by equation (3), the estimated or aligned value of a sheet property at a particular location depends upon the measured value at that location during a current scan as well as the measured value at that location during the immediately preceding scan. More particularly, the estimated or aligned value of a sheet property at any given slice location for a given scan is, according to equation (3), an average of the currently measured value of the sheet property at the slice location and the value at the same slice location measured during the preceding scan. Therefore, according to this alignment method, estimated profiles will lag conventional profiles by one half scan. (For the first scan it can be assumed that the estimated profile equals the measured profile.)

After estimated or aligned values are obtained by equation (3), the respective machine-directional and cross-directional variations in the sheet property can be obtained pursuant to equations (1) and (2) above.

According to yet another alternative methodology, it is assumed that sheet properties do not change rapidly in the cross-direction relative to changes in the machine-direction. Under such an assumption, high-frequency machine-direction values are equated to actual measurement values at slice locations when a scanner first comes on sheet (i.e., during the first scan). Then, after readings are obtained for a second scan, a corrected crossdirection profile is estimated by the methods described above. Next, the average value for the first estimated profile is calculated (where the average value is the average of all points used to estimate the corrected cross-directional profile), and that average value is subtracted from the estimated or aligned values at each slice position to obtain estimates for crossdirectional variations at the slice locations. Then, during the next consecutive scan, those crossdirectional variation values are subtracted from the actual measurements during the scan to obtain values for variations in the machine direction. It should be noted that the subtracted cross-direction variation values are one scan old; however, this fact does not cause substantial inaccuracies in circumstances where cross-direction values vary relatively slowly.

Although the present invention has been illustrated and described in accordance with a preferred embodiment, it should be recognized that variations and changes may be made therein without departing from the invention as set forth in the following claims.

What is claimed is:

1. A method for determining machine-directional variations in a property of a traveling sheet during production, comprising the steps of:
    traversing the travelling sheet with a scanning sensor and taking measurements of a property of the sheet at a plurality of slice locations;
    estimating variations in cross-directional measurement values based upon actual measurements at the plurality of slice locations; and
    then, determining machine-directional variations in the sheet property at each slice location by calculating the difference between the actual measured value and the estimated cross-directional variation for that slice location.

2. A method for determining machine-directional variations in a property of a traveling sheet during production, comprising the steps of:
    repeatedly traversing the travelling sheet with a scanning sensor and during each traverse, taking measurements of a property of the sheet at a plurality of slice locations;
    estimating cross-directional measurement values at reference locations for each scan based upon the actual measurements at the plurality of slice locations;
    for each scan, determining the average of the estimated aligned cross-directional measurement values;
    calculating the cross-directional variations in properties of the sheet at each slide location along the scans by, for each scan, subtracting the average value from the estimated aligned value at each slice location along the scan; and
    during the next scan, determining machine-directional variations in the sheet property at each slice location by calculating the difference between the actual measured value and the calculated cross-directional variation value for that slice location along the prior scan.

3. The method of claim 2, wherein the step of estimating cross-directional measurement values is based upon actual measurements taken during two consecutive traverses of the slice.

4. The method of claim 3, wherein the measurements taken during consecutive traverses are linearly combined to determine estimated aligned measurements.

5. The method of claim 2 wherein the reference locations are true cross-directional scans which are generally regularly spaced in the cross-direction.

6. The method of claim 5, wherein the measured property is the basis weight of the sheet.

7. The method of claim 5, wherein the measured property is the moisture content of the sheet.

8. The method of claim 5, wherein the measured property is the caliper of the sheet.

9. The method of claim 2, wherein the sheet is paper.

10. A method for determining machine-directional variations in a property of a travelling sheet during production, comprising the steps of:
    repeatedly traversing the travelling sheet with a scanning sensor and, during each traverse, taking actual measurements of a property of the sheet at a plurality of slice locations;
    at reference locations, estimating true cross-directional measurement values for each scan based upon the following formula:

$$E_{j,i} = \tfrac{1}{2}(S_j + S_{j+1,i})$$

where E is the estimated aligned value of a sheet property, S is the actual measured value of the sheet property, the subscript i represents the slice location, and the subscript j identifies the scan j;
    determining the average of the estimated cross-directional measurement values for each scan;
    calculating the cross-directional variations in sheet properties at each slice location along the selected scans by, for each scan, subtracting the average value from the estimated aligned value at each slice location along the scan; and
    during the next consecutive scan, determining machine-directional variations in the sheet property at each slice location by calculating the difference between the actual measured value and the calculated cross-directional variation value for that slice location along the prior scan.

11. The method of claim 10 wherein the reference locations are true cross-directional scans which are generally regularly spaced in the crossdirection.

* * * * *